United States Patent
Burger et al.

(10) Patent No.: US 9,737,369 B2
(45) Date of Patent: Aug. 22, 2017

(54) SURGICAL APPARATUS AND PROCEDURE

(75) Inventors: Thorsten Burger, München (DE);
Frank Foley, Leeds (GB); Michal Slomczykowski, Buchrain (CH)

(73) Assignee: DePuy International Ltd., Leeds (GB)

( * ) Notice: Subject to any disclaimer, the term of this patent is extended or adjusted under 35 U.S.C. 154(b) by 1237 days.

(21) Appl. No.: 12/919,839

(22) PCT Filed: Feb. 26, 2009

(86) PCT No.: PCT/GB2009/000512
§ 371 (c)(1),
(2), (4) Date: Dec. 13, 2010

(87) PCT Pub. No.: WO2009/106812
PCT Pub. Date: Sep. 3, 2009

(65) Prior Publication Data
US 2011/0092858 A1    Apr. 21, 2011

(30) Foreign Application Priority Data
Feb. 29, 2008    (GB) .................................. 0803725.1

(51) Int. Cl.
*A61B 5/103*    (2006.01)
*A61B 34/10*    (2016.01)
(Continued)

(52) U.S. Cl.
CPC .............. *A61B 34/10* (2016.02); *A61B 34/20* (2016.02); *A61B 2090/061* (2016.02)

(58) Field of Classification Search
USPC .................... 600/595, 592, 587; 606/90, 102
See application file for complete search history.

(56) References Cited

U.S. PATENT DOCUMENTS 6,002,859 A  * 12/1999  DiGioia et al. ................. 703/11
7,634,306 B2 * 12/2009  Sarin ....................... A61B 5/103
                                                     600/426
(Continued)

FOREIGN PATENT DOCUMENTS

EP          1700574 A1      9/2006
EP          1870053 A2     12/2007
(Continued)

OTHER PUBLICATIONS

GB Search Report GB0803725.1, dated May 30, 2008.
PCT International Search Report and Written Opinion, PCT/GB2009/000512, dated Jul. 21, 2009.

*Primary Examiner* — Michael C Stout
(74) *Attorney, Agent, or Firm* — Wayne C. Jaeschke, Jr.

(57) ABSTRACT

A computer assisted surgery method and apparatus for determining a change in a property of a joint of a patient caused by an arthroplasty procedure is described. The relative position of a first bone and a second bone of the joint is determined with the joint in a first position. The position of a pre-operative center of motion of the joint relative to the first bone is determined. The position of the second bone relative to the pre-operative center of motion is determined using the relative position of the first and second bones. The position of a post-operative center of motion resulting from a prosthetic component to be used in the joint is determined. The position of the second bone relative to the post-operative center of motion is determined. Any change in the property of the joint. is determined from the difference between the position of the second bone relative to the pre-operative center of motion and the position of the second bone relative to the post-operative center of motion.

16 Claims, 5 Drawing Sheets

(51) Int. Cl.
*A61B 34/20* (2016.01)
*A61B 90/00* (2016.01)

(56) References Cited

U.S. PATENT DOCUMENTS

| | | | |
|---|---|---|---|
| 2003/0105470 A1* | 6/2003 | White | 606/102 |
| 2003/0153829 A1 | 8/2003 | Sarin | |
| 2005/0065617 A1* | 3/2005 | Moctezuma de la Barrera | A61B 5/064 606/102 |
| 2005/0119661 A1* | 6/2005 | Hodgson et al. | 606/90 |
| 2005/0149050 A1 | 7/2005 | Stifter | |
| 2005/0203536 A1 | 9/2005 | Laffargue | |
| 2006/0264969 A1* | 11/2006 | Leitner et al. | 606/102 |
| 2006/0293614 A1 | 12/2006 | Radinsky | |
| 2007/0209220 A1* | 9/2007 | Murphy | A61B 5/103 33/512 |
| 2007/0239281 A1* | 10/2007 | Gotte | A61B 90/36 623/20.27 |
| 2007/0249967 A1* | 10/2007 | Buly | A61B 5/1121 600/595 |
| 2008/0045839 A1 | 2/2008 | Drumm | |
| 2008/0051910 A1 | 2/2008 | Kammerzell | |
| 2008/0146969 A1* | 6/2008 | Kurtz | 600/595 |
| 2008/0208081 A1* | 8/2008 | Murphy | A61B 90/36 600/595 |
| 2008/0255442 A1* | 10/2008 | Ashby | A61B 5/103 600/407 |
| 2008/0319448 A1* | 12/2008 | Lavallee et al. | 606/102 |
| 2010/0030231 A1* | 2/2010 | Revie | A61B 90/36 606/130 |
| 2014/0135791 A1* | 5/2014 | Nikou et al. | 606/130 |
| 2014/0180290 A1* | 6/2014 | Otto et al. | 606/80 |

FOREIGN PATENT DOCUMENTS

| | | |
|---|---|---|
| WO | WO 2005000140 A2 | 1/2005 |
| WO | WO 2005023110 A1 | 3/2005 |
| WO | WO 2006129087 A1 * | 12/2006 |
| WO | WO 2007147235 A1 | 12/2007 |

\* cited by examiner

SURGICAL APPARATUS AND PROCEDURE

CROSS REFERENCE TO RELATED PCT APPLICATION

This application is a National Stage 35 U.S.C. 371 of International Patent Application PCT/GB2009/000512, filed Feb. 26, 2009.

The present invention relates generally to surgery, and in particular to methods, computer implemented methods and computer assisted surgery apparatus for orthopaedic arthroplasty procedures. The invention is particularly applicable to arthroplasty procedures for ball and socket joints, such as hips and shoulders.

BACKGROUND OF THE INVENTION

In orthopaedic arthroplasty procedures, it is generally desirable to be able to determine the outcome of the procedure. For example, the intention of the procedure may be to recreate the state of the joint immediately prior to the procedure, the intention may be to put the joint into an original ideal or preferred state, or the intention may be to put the joint into a state which is preferred for the particular patient's anatomy or for other reasons. Whatever the specific intention of any particular procedure it is generally of used to be able accurately to determine the effect of the procedure on the joint.

For example, when carrying out a hip procedure, it is often desirable to be able to determine any changes in the leg length and/or offset caused by the procedure.

U.S. Pat. No. 6,711,431 describes a computer assisted surgical procedure which can be used to determine any change in leg length and offset. The system includes a locating system and a computer and a software module, executable on the computer. A pelvic tracking marker is fixed to the pelvic bone and a femoral tracking marker is securely attached to the femur of the patient. The position of the femur is determined before the operation with the femur in a specific reference position. The position of the femur in the same reference position is determined after the operation and the system detects changes in leg length and femoral offset. However, the accuracy of the determination depends on whether the femur has been returned to the same reference position and so in practice is subject to errors.

It is therefore desirable to provide a method having improved accuracy and reliability of determination of any change in a joint after a surgical procedure on the joint.

BRIEF SUMMARY OF THE INVENTION

According to a first aspect of the present invention, there is provided a method for determining a change in a property of a joint of a patient caused by an arthroplasty procedure carried out on the joint, the method being carried out by a computer assisted surgery system, and wherein the joint comprises a first bone and a second bone, the method comprising: determining the relative position of the first bone and the second bone with the joint in a first position; determining the position of a pre-operative centre of motion of the joint relative to the first bone; determining the position of the second bone relative to the pre-operative centre of motion using the relative position of the first bone and second bone; determining the position of a post-operative centre of motion of the joint resulting from a prosthetic component to be used in the joint; determining the position of the second bone relative to the post-operative centre of motion; and determining the difference between the position of the second bone relative to the pre-operative centre of motion and the position of the second bone relative to the post-operative centre of motion to determine any change in the property of the joint.

As the method determines the relative positions of the bones toward the beginning of the method, and as the centre of motion is common to the bones of the joint, it is possible to determine how changes to either or both of the bones by a prosthetic implant will change the joint as the original relationship between the bones is known.

The method can be applied to any joint having a common centre of motion for the bones of the joint. Preferably, the centre of motion is a centre of rotation.

The method can be applied to a variety of different types of joints. Preferably, the joint is a ball and socket type joint. The joint can be a hip joint or a shoulder joint.

The property of the joint can be any geometric property associated with the joint, such as a direction of a part of the joint, a position of a part of the joint or a length of a part of the joint.

When the joint is a hip, the first bone can be a part of the pelvis and the second bone can be the femur.

When applied to the hip joint, the property of the joint can be the leg length and/or the offset The property can be a relative position of the first and second bones, such as the combined anteversion when in the first position.

The method can further comprise capturing the positions of a plurality of anatomical points generally defining a coronal plane of the patient's body. The position of the coronal plane can be determined from the plurality of anatomical points. The difference between the position of the second bone relative to the pre-operative centre of motion and the position of the second bone relative to the post-operative centre of motion can be projected onto the coronal plane to determine the leg length and/or offset. The leg length can be the difference in a inferior-superior direction of the patient. The offset can be the difference in the medial-lateral direction of the patient.

Determining the position of a post-operative centre of motion of the joint resulting from a prosthetic component to be used in the joint can further comprise determining the position of the post-operative centre of motion of the first bone relative to a trackable marker attached to the first bone.

Determining the position of the second bone relative to the post-operative centre of motion can further comprise determining the position of the post-operative centre of motion of the second bone relative to a trackable marker attached to the second bone.

Determining the difference between the position of the second bone relative to the pre-operative centre of motion and the position of the second bone relative to the post-operative centre of motion can include mapping the position of the post-operative centre of motion of the second bone onto the post-operative centre of motion of the first bone.

The post-operative centre of motion can be defined by a property of a prosthetic implant. The property of the implant can be its size, position or an aspect of its geometry. For example, the property of the implant can be the centre of rotation of an acetabular cup or the centre of rotation for a head of a femoral implant.

The method can further comprise determining whether any change in the property of the joint is acceptable. If not, then a change to a property of the prosthetic component to be used in the joint which will make the property of the joint closer to a target property can be determined. The change in the property of the prosthetic component, or a part of a prosthetic component, can include a number of attributes, and combinations of such attributes, of the component, such as the type of implant, the size of the implant, the position of the implant in the bone and the geometry of the implant.

The target property can be a pre-operative property of the joint or can be a preferred property of the joint such as a property which will correct, ameliorate or reduce a disease state or deformity of the joint.

The method can further comprise re-determining the change in the property of the joint resulting from the change to the property of the prosthetic component.

The method can further comprise automatically identifying a change in the property of the prosthetic component which will minimise the change in the property of the joint.

A further aspect of the invention provides a computer assisted surgery system for determining a change in a property of a joint of a patient caused by an arthroplasty procedure carried out on the joint, the system comprising at least one data processing device in communication with at least one storage device, the storage device storing instructions executable by the data processing device to cause the computer assisted surgery system to carry out any of the method aspects of the invention.

A further aspect of the invention provides a computer program product comprising a computer readable medium storing computer readable instructions executable by a data processing device to carry out any of the method aspects of the invention.

BRIEF DESCRIPTION OF THE DRAWINGS

An embodiment of the invention will now be described, by way of example only, and with reference to the accompanying drawings, in which.

Figure 1A:
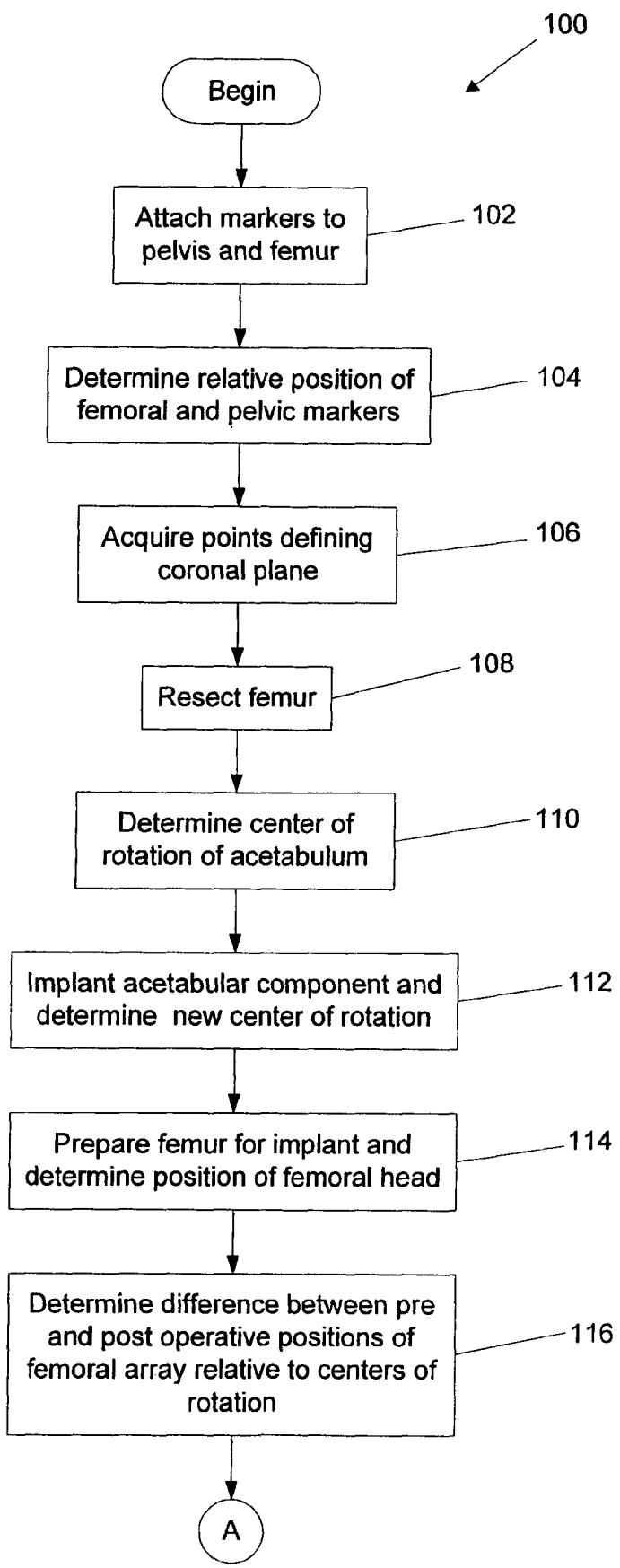
FIGS. 1A and 1B show a process flow chart illustrating aspects of a surgical method and a computer implemented method, both according to the invention.

Similar items in different Figures share common reference numerals unless indicated otherwise.

DETAILED DESCRIPTION OF THE INVENTION

The invention will be described with reference to a hip joint, but it will be appreciated that it can be applied to other types of joints and in particular to other ball and socket type joints, such as the shoulder. The invention can in general be applied to any joint where there is some functional entity created by at least two bones. For example in the shoulder joint the invention can be applied to the centre of shoulder rotation, for the knee joint the invention can be applied to the joint line, for the ankle joint the invention can be applied to the joint line, and for the elbow the invention can be applied to the centre of rotation (off joint) and also the joint line.

The invention provides an accurate and reliable way to determine any changes in the geometry of the joint, such as the leg length and/or off set. The aim of the surgical procedure might be to restore the bio-mechanical function of a patient's hip by restoring the pre-operative centre of rotation as well as the leg length and offset. The invention is realised as part of a computer assisted surgery (CAS) based procedure using a CAS system, including a tracking system which allows the positions of the patient's limbs or other body parts to be tracked within a reference frame of the tracking system. Various types of tracking technologies are known and the details or specific tracking technology used are not important. The embodiment described below uses an optical or infra-red wireless tracking system in which marker arrays are attached to the patient to allow the positions of the body parts to be tracked.

The invention will be described below in terms of a CAS workflow carried out by a surgeon. It will be appreciated that at various stages in the workflow, the CAS system will carry out various calculations and procedures under control of suitable software as counterpart steps of a method of operation of a CAS system. Hence aspects of the invention relate to the surgical procedure, the data processing operations carried out by the CAS system, a suitably programmed CAS system and computer programs and computer program products embodying the instructions for controlling the CAS system.

Figure 1B:
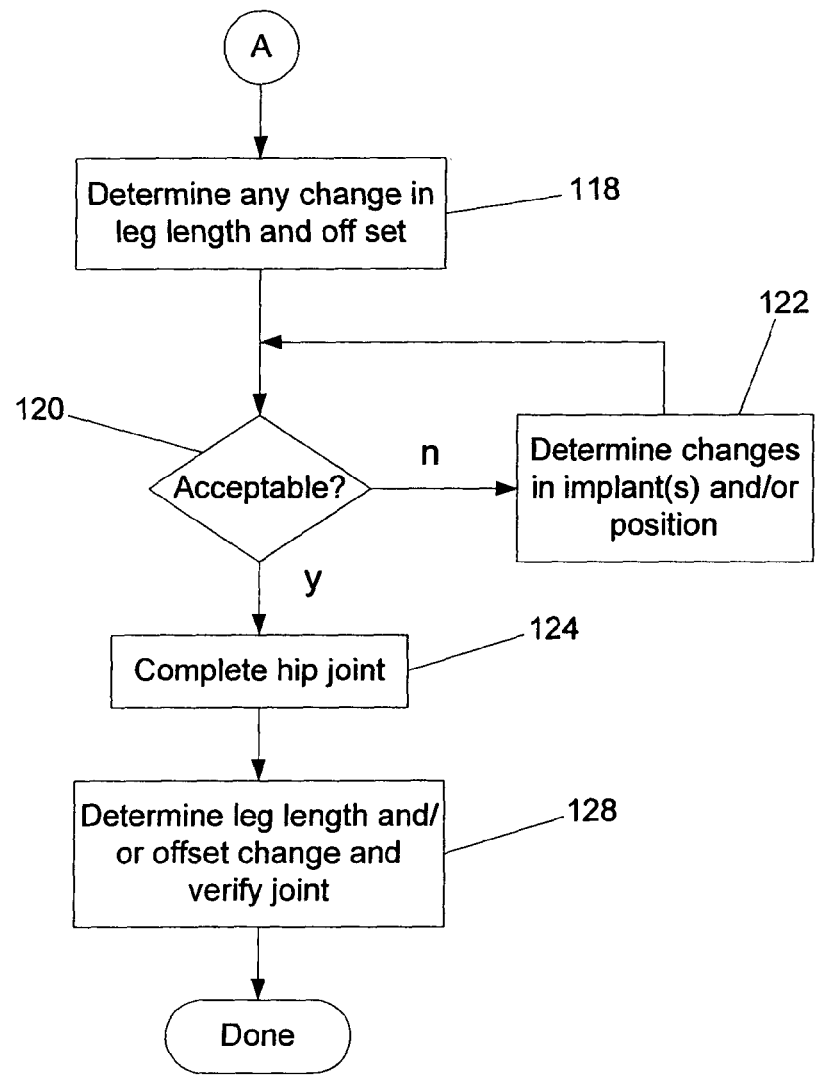
Figure 2:
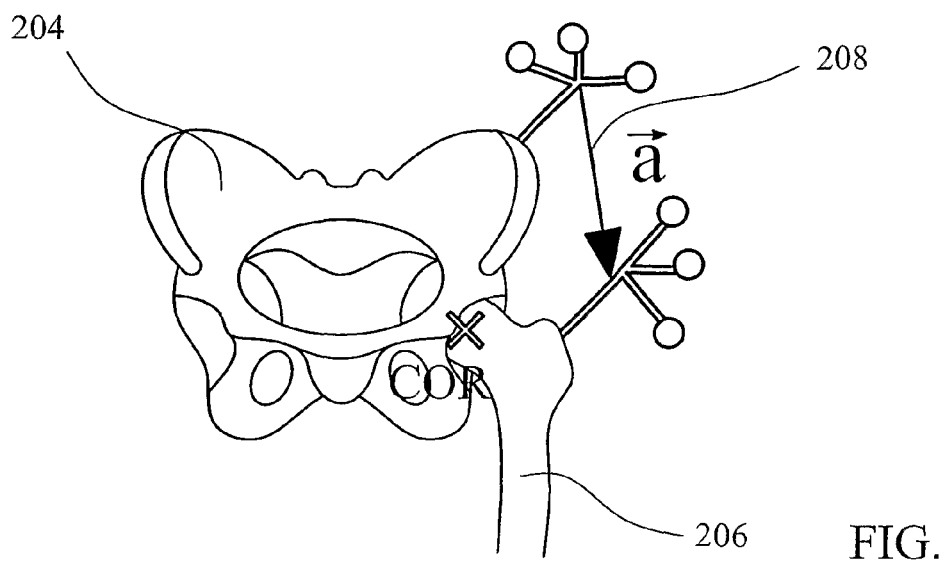
FIG. 2 shows a schematic frontal view of a pelvis and femur illustrating the relative positions of the pelvic and femoral markers.

FIGS. 1A and 1B show a flow chart illustrating a CAS method 100 carried out by a surgeon using a CAS system according to the invention. At step 102, the surgeon attaches a first trackable marker 202 (the pelvic marker) to the patient's pelvis 204 as illustrated schematically in FIG. 2. The surgeon also attaches a second trackable marker 205 (the femoral marker) to a proximal part of the patient's femur 206 as also shown in FIG. 2. The pelvic and femoral markers are each distinguishable by the CAS system. The surgeon places the limb, in this instance the leg, in full extension, which can be done with the patient either supine or in a lateral position. The CAS system is then instructed to determine and store the relative positions of the pelvic and femoral markers in the reference frame or co-ordinate system of the CAS system at step 104. The relative positions of the pelvic and femoral markers is represented by vector a 208 in FIG. 2.

Figure 3:
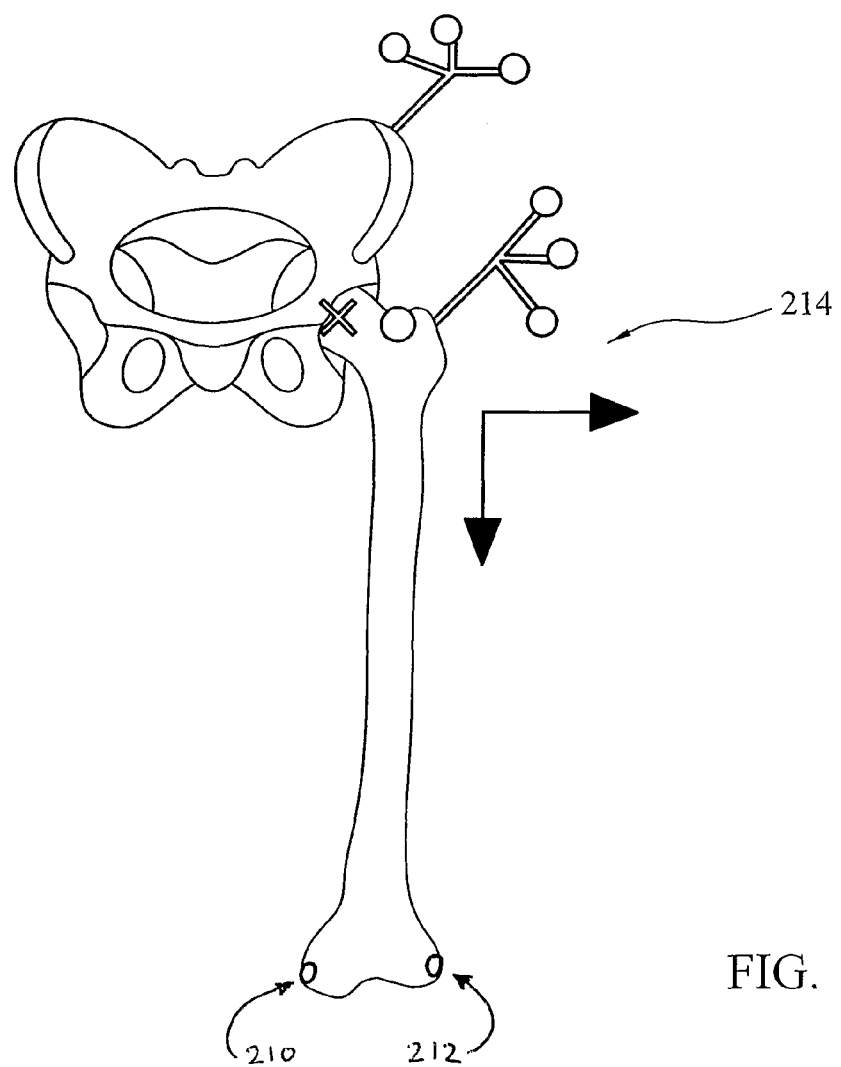
FIG. 3 shows a schematic frontal view of the pelvis and femur illustrating the capture of anatomical positions defining a plane of the body.

Then at step 106, the surgical site is opened by the surgeon and the surgeon captures the positions of a number of anatomical points which are used roughly to define the coronal plane of the patient. For example, the surgeon can use a trackable pointer to identify the positions of a number of anatomical points and the CAS system captures the positions of those points in its reference frame. Before making the incision, the surgeon can capture the positions of the epicondylar points 210, 212 on each side of the femur as illustrated in FIG. 3, and, after the incision, the position of the greater trochanter or the piriformis fossa point 214. These points, together with the later acquired centre of rotation (COR) are used to establish a rough coronal plane that is used in the final leg length and offset change calculation.

In other embodiments, different ways of determining the coronal plane can be used which are generally known in the art, such as pelvic plane registration or intra-operative imaging.

Figure 4:
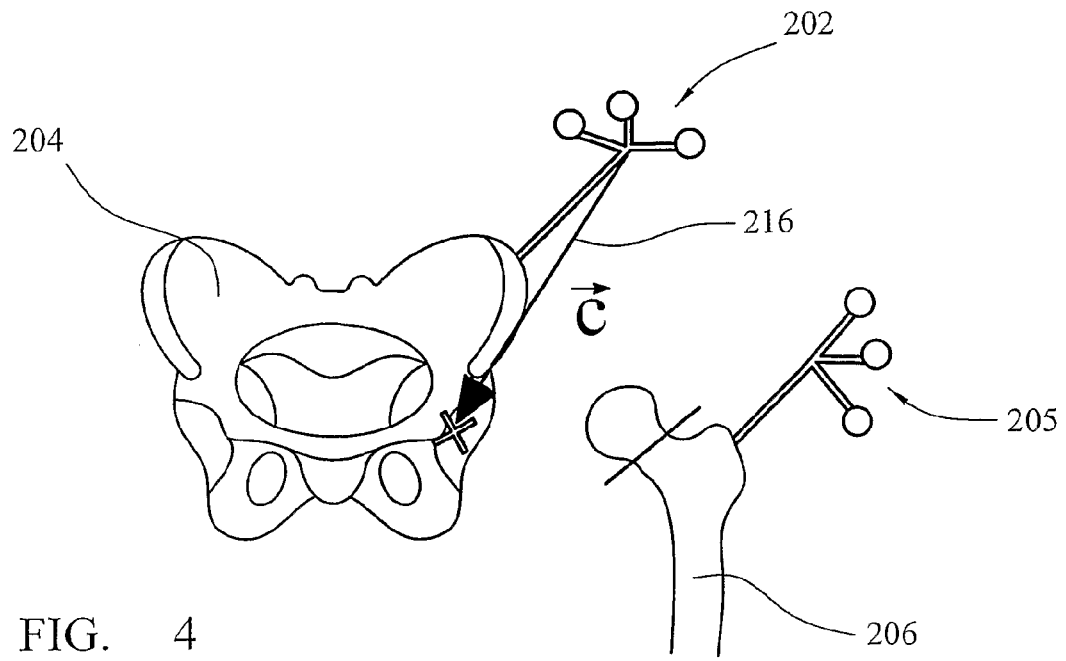
FIG. 4 shows a schematic frontal view of the pelvis and femur illustrating the determination of the pre-operative centre of rotation and resection of the femur.

Then the hip joint is separated and at step 108, the femur is resected to prepare for the prosthetic implant, for example, by removing the femoral head as illustrated in FIG. 4. It will be appreciated that the precise resection will depend on the type of prosthetic implant to be used in the surgical procedure.

At step 110, the position of the centre of rotation (COR) of the acetabular cup is determined and captured in the reference frame of the CAS system. This can be achieved in a number of ways, for example, by using a special templating tool or a navigated insertion tool with a trial cup. The CAS system tracks the position of the templating tool or navigated insertion tool and captures the position of the pre-operative COR of the pelvis. The COR is pre-operative in the sense that although it is captured during the operation, the acetabulum has not yet been operated on and so it is anatomically the same as before the operation began.

In other embodiments, different approaches to determining the centre of rotation can be used. For example, a trackable pointer can be moved over the surface of the acetabulum to "paint" the surface of the acetabulum from which the shape of the acetabulum can be reconstructed and the COR determined. Alternatively, the first bone can be moved relative to the second bone and the COR determined by tracking the position of the second bone as it is pivoted in order to determine the COR.

Figure 5:
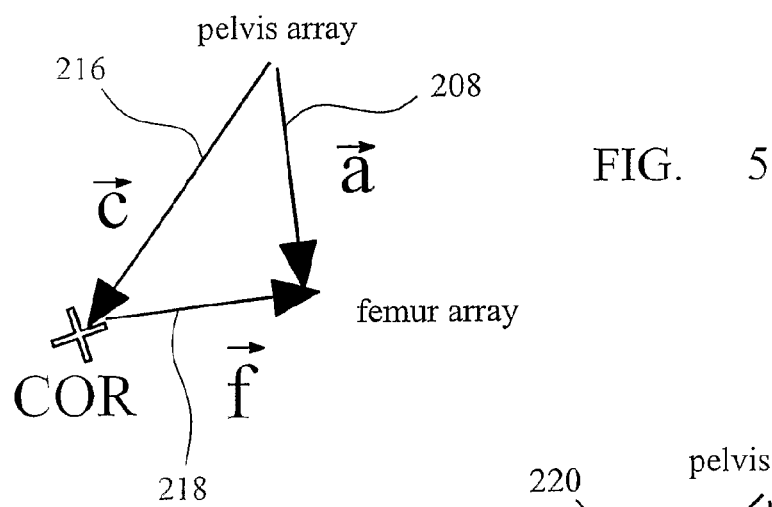
FIG. 5 shows a vector diagram illustrating the relationships between the pelvic marker, femoral marker and pre-operative centre of rotation.

The CAS system also determines the position of the pelvic marker when the position of the COR is determined so that the position of the COR relative to the pelvic marker can be determined in the reference frame of the tracking system. The position of the pre-operative COR relative to the pelvic marker is represented by vector c 216 in FIG. 4. As the relative position of the pelvic and femoral markers was determined at step 104, the virtual position of the pre-operative COR relative to the femur, when the hip joint was still assembled, can be determined from the vector sum a+c and is vector f 218 illustrated in FIG. 5.

Figure 6:
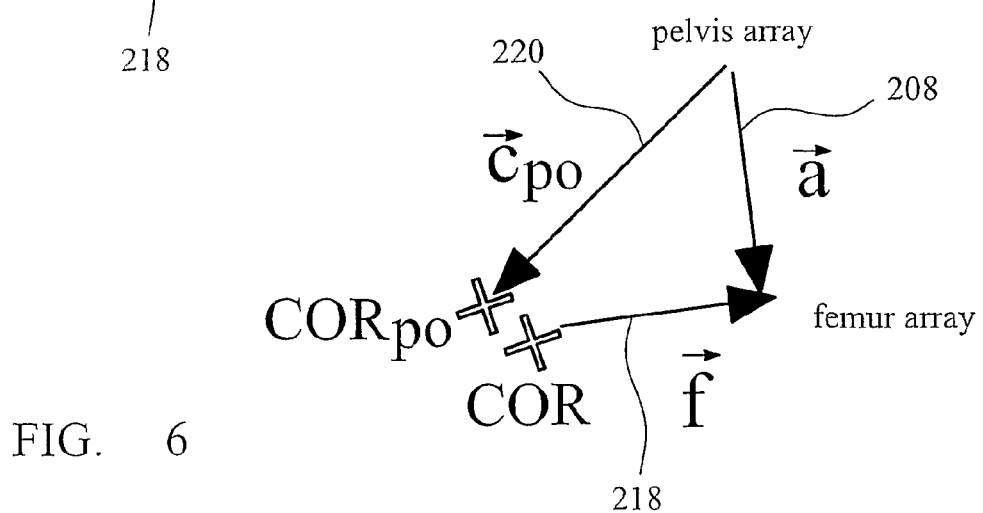
FIG. 6 shows a vector diagram similar to FIG. 5 and including the post-operative centre of rotation.

Then at step 112, the acetabulum is prepared and the acetabular prosthetic component is implanted into the pelvis. This will give rise to a new post-operative centre of rotation $COR_{po}$ for the acetabulum. The position of $COR_{po}$ is then determined by the CAS system relative to the pelvic marker, as represented by vector $c_{po}$ 220 in FIG. 6.

Figure 7:
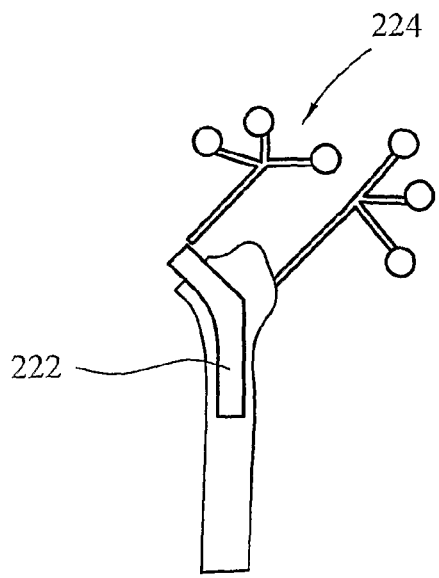
FIG. 7 shows a schematic frontal view of the femur illustrating navigated positioning of the femoral implant.

Then at step 114, the femur is prepared to receive the femoral prosthetic component 222 as illustrated in FIG. 7. The position of the centre of the head of the femoral implant 222 is then determined relative to the position of the femoral marker 205. This can be done in a number of ways, for example by attaching a marker 224 to the prosthetic femoral head, as illustrated in FIG. 7, or by navigating a broach tool so that the position of the cavity accepting the implant is known and hence the position of the head of the implant once implanted will be known. The centre of the head of the femoral implant is the centre of rotation for the femur and will also be the centre of rotation for the joint once re-assembled, as the head is designed to work with the acetabular cup component.

When the invention is applied to the shoulder joint, it will be appreciated that the 'ball and socket' do not necessarily have an identical COR (as the corresponding 'head' and 'cup' of the shoulder joint have different radii), but the principle of the invention can still be applied if pre- and post-operatively the same COR (either that of the ball or the socket) is used.

Figure 8:
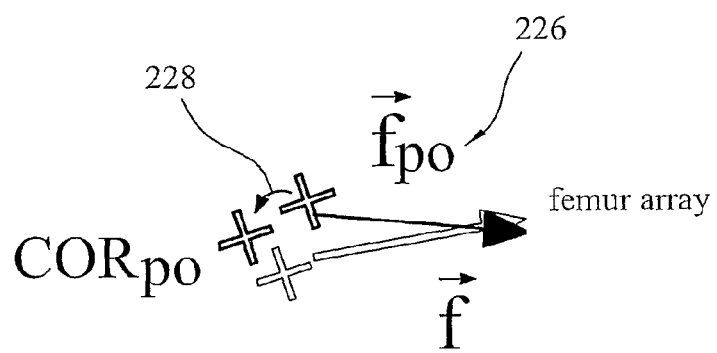
FIG. 8 shows a vector diagram illustrating the relationships between the pelvic post-operative centre of rotation, pre-operative position of the femur relative to the pre-operative centre of rotation and post-operative position of the femur relative to the femoral implant centre of rotation.

The relative position between the post-operative centre of rotation of the femoral component and the femoral marker is determined and is represented by vector $f_{po}$ 226 in FIG. 8.

Figure 9:
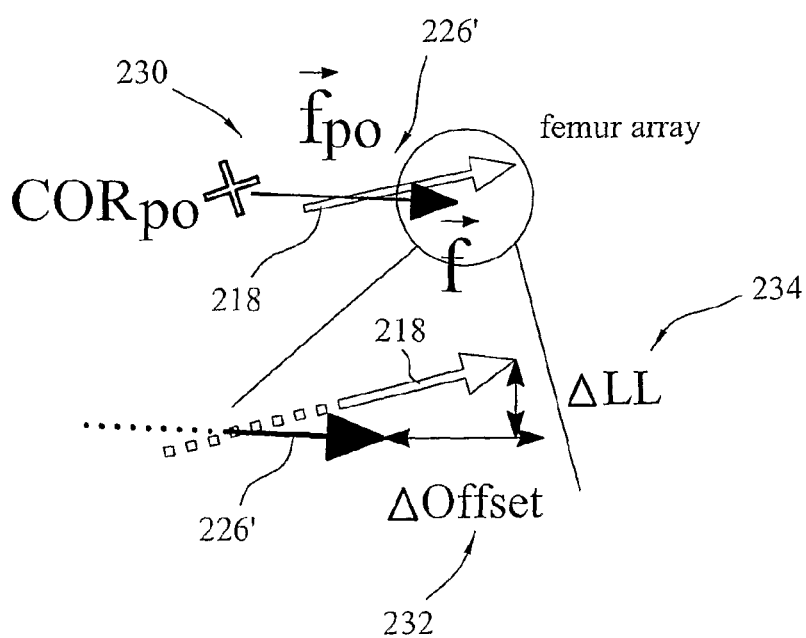
FIG. 9 shows a vector diagram for the reconstructed hip joint illustrating the change in leg length and offset derived from the pre-operative femoral position and the post-operative femoral position.

Then at step 116 the difference between the pre-operative position of the femur relative to the pre-operative centre of rotation and the post-operative position of the femur relative to the post operative centre of rotation is used to determine any changes in leg length and offset. Since in the assembled joint, the femoral centre of rotation will be identical to the acetabular centre of rotation for the prosthetic joint, the vector $f_{po}$ is simply transferred or mapped, as illustrated by arrow 228, onto $COR_{po}$ so that the situation illustrated in FIG. 9 is arrived at. FIG. 9, includes a magnified view of the relevant parts of the vectors. As illustrated in the magnified view in FIG. 9, the difference between $f_{po}$ 226' for the common post-operative centre of rotation and the pre-operative relative position of the femur f 218, when projected onto the coronal plane in the medial-lateral direction and the superior-inferior direction, give any change in offset 232 and leg length 234, respectively.

Further the component of the difference of the vectors in the direction perpendicular to the coronal plane can also be determined and gives any change in the anterior-posterior direction. This itself can be used or can be used to calculate any relevant angular properties of the joint such as the anteversion.

Once any change in leg length or offset or in the anterior-posterior direction has been determined at step 118, it can be determined whether those changes are acceptable or not at step 120. For example, the CAS system may use threshold values or an expert system to determine whether the changes are acceptable or not. In another embodiment, the surgeon may decide that the changes are acceptable or not. If the CAS system determines at step 120 that either or both of the changes are not acceptable, then at step 122 the CAS system determines a modification to one or both of the implants which will reduce the change or changes. For example, the CAS system may determine that an implant of a different size, e.g. smaller or larger, may help reduce the change in offset and/or leg length. Additionally, or alternatively, the CAS system may determine that a different implant position may help reduce the change in offset and/or leg length. Additionally, or alternatively, the CAS system may suggest other modifications to the implants, e.g., different combinations of liner and/or neck and/or head of the femoral component. This is helpful to reduce changes that result from broaching of the femur.

If one of the joint properties is the combined cup and stem anteversion, then modular necks or other geometries of the artificial joint can be suggested to change anteversion.

The method can then be generally repeated using the modified implants until it is determined that the change in leg length and/or off set are acceptable as sufficiently closely restoring the patient to their original condition. Then the hip joint is reduced at step 124 using the implant configuration selected in order to minimize any changes in leg length and offset. Finally at step 128, the change in leg length and offset for the reduced hip joint are determined in order to verify the acceptability of the joint.

In the above described embodiment, the target property of the joint is the pre-operative state of the joint. However, in other embodiments, the target property of the joint may not be to simply recreate the immediately pre-operative state of the joint. For example, the intention of the procedure may be to correct a disease state in which case the joint may need to be reconstructed to be closer to a particular preferred state. That may involve increasing or decreasing any of the properties of the joint to be closer to a target property which may be different to the immediately pre-operative property of the joint.

For example, for whatever reason, a target property of the joint may be to make the joint, e.g. x mm longer, in which cases changes to the prostheses and/or their positions may be determined which make the property of the joint closer to this target property.

Generally, embodiments of the present invention employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium. Examples of program instructions include both machine code, such as produced by a compiler, and files containing higher level code that may be executed by the computer using an interpreter.

It will also be appreciated that the invention is not limited to the specific combinations of structural features, data processing operations, data structures or sequences of method steps described and that, unless the context requires otherwise, the foregoing can be altered, varied and modified. For example different combinations of structural features can be used and features described with reference to one embodiment can be combined with other features described with reference to other embodiments. Similarly the sequence of the method steps can be altered and various actions can be combined into a single method step and some methods steps can be carried out as a plurality of individual steps. Also some of the structures are schematically illustrated separately, or as comprising particular combinations of features, for the sake of clarity of explanation only and various of the structures can be combined or integrated together or different features assigned to other structures. One of ordinary skill in the art would recognize other variants, modifications and alternatives in light of the foregoing discussion.

The invention claimed is:

1. A method for determining a change in at least one property of a hip joint of a patient caused by a surgical arthroplasty procedure carried out on the joint, the method being carried out by a computer assisted surgery system comprising a tracking system, the tracking system comprising at least a first and a second trackable marker, the computer assisted surgery system comprising at least one data processing device in communication with at least one storage device, and wherein the joint comprises a pelvis to which the first trackable marker is attached and a femur to which the second trackable marker is attached, the method comprising the steps of:

using the at least one data processing device during the surgical arthroplasty procedure to determine a position of one or both of the first and second trackable markers in order to determine intra-operatively one or all of the following:
(a) prior to separating the hip joint, with the hip joint in a first position, the position of the femur relative to the pelvis;
(b) the position of a pre-operative center of motion of the hip joint relative to the pelvis;
(c) the position of the femur relative to the pre-operative center of motion using the position of the femur relative to the pelvis;
(d) the position of a post-operative center of motion of the hip joint resulting from a prosthetic component to be used in the hip joint; and
(e) the position of the femur relative to the post-operative center of motion;
storing intra-operatively at least one of the positions determined in substeps (a)-(e) in the storage device; and
using the at least one data processing device to determine infra-operatively the difference between the position of the femur relative to the pre-operative center of motion and the position of the femur relative to the post-operative center of motion to determine any change in the at least one property of the hip joint.

2. The method of claim 1, wherein the pre-operative center of motion is a pre-operative center of rotation and the post-operative center of motion is the post-operative center of rotation.

3. The method of claim 1, wherein the at least one property of the hip joint is one of a leg length and an off set.

4. The method of claim 1, wherein the at least one property of the hip joint includes or is a distance in the anterior-posterior direction.

5. The method of claim 1, wherein the at least one property of the hip joint is the anteversion of the hip joint.

6. The method of claim 3, and further comprising:
capturing the positions of a plurality of anatomical points generally defining a coronal plane of the patient's body;
determining the position of the coronal plane from the plurality of anatomical points; and
projecting the difference between the position of the femur relative to the pre-operative center of motion and the position of the femur relative to the post-operative center of motion onto the coronal plane to determine the leg length and offset.

7. The method of claim 1, wherein determining the position of a post-operative center of motion of the hip joint resulting from a prosthetic component to be used in the hip joint further comprises determining the position of the post-operative center of motion of the pelvis relative to the first trackable marker.

8. The method of claim 7, wherein determining the position of the femur relative to the post-operative center of motion further comprises determining the position of the post-operative center of motion of the femur relative to the second trackable marker.

9. The method of claim 8, wherein determining the difference between the position of the femur relative to the pre-operative center of motion and the position of the femur relative to the post-operative center of motion includes mapping the position of the post-operative center of motion of the femur onto the post-operative center of motion of the pelvis.

10. The method of claim 1, wherein the post-operative center of motion is defined by a property of a prosthetic implant.

11. The method of claim 1, and further comprising:
determining whether any change in the at least one property of the hip joint is acceptable, and if not, then identifying a change to a property of the prosthetic component to be used in the hip joint which will make the at least one property of the hip joint closer to a target property of the hip joint.

12. The method of claim 11, further comprising:
re-determining the change in the at least one property of the hip joint resulting from the change to the property of the prosthetic component.

13. The method of claim 11, where the target property of the hip joint is a pre-operative property of the hip joint.

14. A computer assisted surgery system for determining a change in a property of a hip joint of a patient caused by an arthroplasty procedure carried out on the hip joint, the system comprising at least one data processing device in communication with at least one storage device, the storage device storing instructions executable by the data processing device to cause the computer assisted surgery system to carry out the method of claim 1.

15. A computer program product comprising a non-transitory, tangible computer readable medium storing computer readable instructions executable by a data processing device to carry out the method of claim 1.

16. The method of claim 1, further comprising the step of, prior to the substep (d) determining step, cutting the femoral head.

* * * * *